US012599641B2

(12) United States Patent
Lee et al.

(10) Patent No.: US 12,599,641 B2
(45) Date of Patent: Apr. 14, 2026

(54) PROBIOTIC COMPOSITION FOR IMPROVING SOY PROTEIN PROTEOLYSIS AND AMINO ACID PRODUCTION ACTIVITY

(71) Applicant: LACTOMASON CO., LTD., Jinju-si (KR)

(72) Inventors: Young Jin Lee, Seoul (KR); Woo Hyun Jung, Incheon (KR); So Lim Shin, Anyang-si (KR); Minn Sohn, Jinju-si (KR)

(73) Assignee: LACTOMASON CO., LTD., Jinju-si (KR)

( * ) Notice: Subject to any disclaimer, the term of this patent is extended or adjusted under 35 U.S.C. 154(b) by 78 days.

(21) Appl. No.: 18/675,254

(22) Filed: May 28, 2024

(65) Prior Publication Data

US 2025/0186518 A1 Jun. 12, 2025

Related U.S. Application Data

(63) Continuation of application No. PCT/KR2024/006324, filed on May 10, 2024.

(30) Foreign Application Priority Data

Dec. 8, 2023 (KR) ........................ 10-2023-0177852

(51) Int. Cl.
*A61K 35/747* (2015.01)
*A61K 35/00* (2006.01)
*A61P 1/14* (2006.01)

(52) U.S. Cl.
CPC .............. *A61K 35/747* (2013.01); *A61P 1/14* (2018.01); *A61K 2035/115* (2013.01)

(58) Field of Classification Search
CPC .... A61K 35/747; A61K 2035/115; A61P 1/14
See application file for complete search history.

(56) References Cited

U.S. PATENT DOCUMENTS

2003/0235559 A1 12/2003 Sobol et al.

FOREIGN PATENT DOCUMENTS

| KR | 10-2021-0067689 A | 6/2001 |
| KR | 10-2020-0050002 A | 5/2020 |
| KR | 10-2268124 B1 | 6/2021 |
| KR | 10-2022-0046329 A | 4/2022 |
| KR | 10-2023-0040252 A | 3/2023 |
| KR | 10-2023-0040255 A | 3/2023 |
| KR | 10-2540559 B1 | 6/2023 |
| KR | 102578662 B1 | 9/2023 |

OTHER PUBLICATIONS

Laura Aguirre, Marisa S. Garro, Graciela Savoy de Giori, "Enzymatic hydrolysis of soybean protein using lactic acid bacteria", Food Chemistry, vol. 111, Issue 4, 2008, p. 976-982, ISSN 0308-8146, doi.org/10.1016/j.foodchem.2008.05.018. (Year: 2008).*

* cited by examiner

*Primary Examiner* — Kade Ariani
(74) *Attorney, Agent, or Firm* — NKL Law; Jae Youn Kim

(57) ABSTRACT

The present disclosure can improve the degree of soy protein proteolysis and the ability to produce valine, isoleucine, and leucine, which are branched-chain amino acids, as well as other amino acids, such as threonine, glycine, tyrosine, and lysine. Accordingly, the present disclosure can prevent sarcopenia and has antioxidant activity. Also, the present disclosure can maintain protein metabolic balance and relieve sarcopenia by muscle synthesis.

The self-aggregation, hydrophobicity, and intestinal adhesion of a mixed strain is improved compared to a case where a single strain used for the mixed strain is used. Therefore, when the mixed strain of the present disclosure is ingested, the strain can remain for a long time in the intestine.

14 Claims, 2 Drawing Sheets

PROBIOTIC COMPOSITION FOR IMPROVING SOY PROTEIN PROTEOLYSIS AND AMINO ACID PRODUCTION ACTIVITY

TECHNICAL FIELD

The present disclosure relates to a mixed strain composition with soy protein proteolysis activity and amino acid production activity, and more particularly, to a mixed strain of *Limosilactobacillus fermentum* LM1020 (KCCM12918P) and *Lactobacillus acidophilus* LM1060 (KCCM12625P) and a composition containing the same as an active ingredient.

BACKGROUND

Muscle loss associated with aging and an increase in obese population caused by westernized diet and less physical activity are important from a public health perspective. Protein intake is helpful in maintaining muscle while suppressing muscle loss associated with aging, and intake of sufficient amounts of proteins by all age groups is known to reduce the risk of sarcopenia and diseases caused by obesity.

Representative dietary sources of proteins can be classified into animal proteins, such as milk, eggs, beef, pork, chicken, and fish, and plant proteins, such as soybeans and grains. Milk protein among the animal protein sources has an excellent composition of essential amino acids, such as leucine, isoleucine, methionine, etc. Also, whey protein produced by concentrating whey, which is a liquid by-product separated from milk during a cheese or casein production stage, is highly bioavailable and quickly absorbed and thus has been consumed widely as a protein supplement. However, the whey protein is deficient in dietary fiber and high in fat and cholesterol, and, thus, careful attention needs to be paid to intake during weight control. Also, the whey protein contains lactose. When lactose intolerance is caused by deficiency of lactase, a digestive enzyme that hydrolyzes lactose, the lactose is not hydrolyzed in the digestive system after intake of the whey protein, which may result in gastrointestinal disorders, such as stomachache, diarrhea and vomiting.

Recently, an eco-friendly and sustainable diet has gained attention worldwide. Thus, foods substituted for animal materials are being actively developed and interest in plant proteins is increasing.

Conventional examples of probiotic compositions having proteolysis activity may include a food composition and health functional food containing *Lactobacillus casei* IDCC 3451 having proteolysis activity (Korean Patent Laid-open Publication No. 10-2023-0040252). However, there is still a need for development and studies on compositions capable of overcoming the disadvantages of the prior art upon proteolysis and intake of plant-derived proteins.

DISCLOSURE OF THE INVENTION

Problems to be Solved by the Invention

The present disclosure is conceived to provide a mixed strain with soy protein proteolysis activity or amino acid production activity.

Means for Solving the Problems

An aspect of the present disclosure provides a mixed strain containing *Limosilactobacillus fermentum* LM1020

(Accession Number: KCCM12918P) and *Lactobacillus acidophilus* LM1060 (Accession Number: KCCM12625P), and the mixed strain is capable of improving the degree of soy protein proteolysis.

Another aspect of the present disclosure provides a food composition, a health functional food composition, an infant formula composition, and a pharmaceutical composition for preventing or relieving sarcopenia, containing one or more of the mixed strain of the first aspect or a culture, lysates and extracts of the mixed strain as an active ingredient.

Effects of the Invention

According to any one of the above-described means for solving the problems of the present disclosure, it is possible to improve the degree of soy protein proteolysis and also possible to prevent or relieve sarcopenia.

BEST MODE FOR CARRYING OUT THE INVENTION

Figure 1:
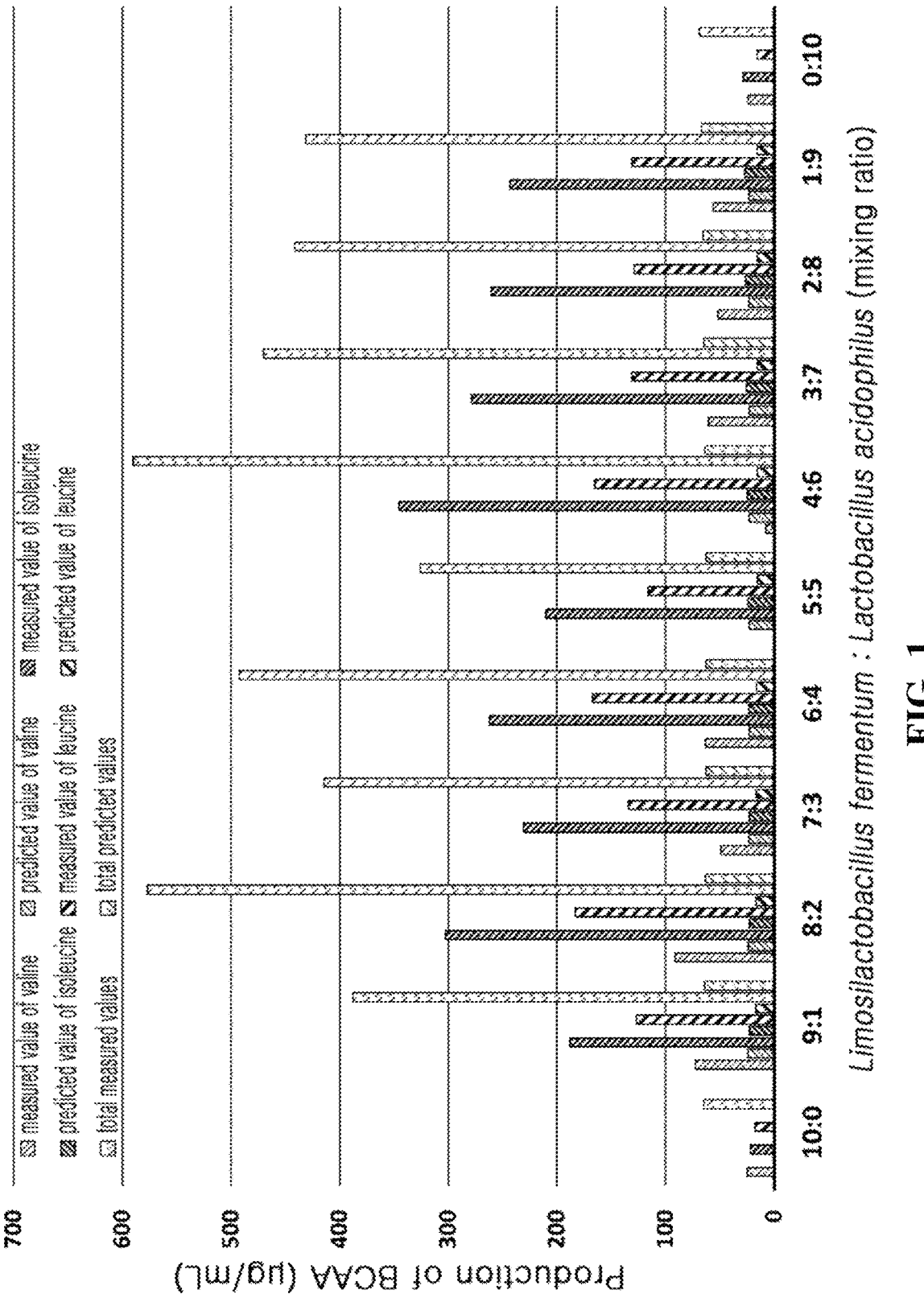
FIG. 1 shows the result of confirming that a mixed strain of the present disclosure has the ability to produce valine, isoleucine, and leucine for each mixing ratio, according to Example 2.

Hereafter, examples of the present disclosure will be described in detail with reference to the accompanying drawings so that the present disclosure may be readily implemented by a person with ordinary skill in the art. However, it is to be noted that the present disclosure is not limited to the examples but can be embodied in various other ways. In the drawings, parts irrelevant to the description are omitted for the simplicity of explanation, and like reference numerals denote like parts throughout the whole document.

Throughout the whole document, the term 'comprises or includes' and/or 'comprising or including' used in the document means that one or more other components, steps, operation and/or existence or addition of elements are not excluded in addition to the described components, steps, operation and/or elements unless context dictates otherwise.

Throughout the whole document, the term "mixing ratio" refers to a ratio of *Limosilactobacillus fermentum* LM1020: *Lactobacillus acidophilus* LM1060.

Throughout the whole document, a "culture" may refer to a whole medium including a strain itself, an extract of the strain, a metabolite of the strain, or an extra nutrient obtained by culturing the strain in a nutrient-supplied medium for a certain period of time, and may also include a culture solution in which the strain is removed after the strain culture. Also, a concentrate of the whole medium or culture medium, and a dry product of the concentrate may be included. Specifically, the culture of the present invention may be a medium easily selected by a person skilled in the art according to the purpose among media used for culturing microorganisms, for example, MRS (de MAN, ROGOSA and SHARPE) or BL medium, but is not limited thereto as long as the strain of the present invention may be cultured.

Throughout the whole document, 'lysate' may mean a solution or suspension of an aqueous medium of a cell of a microorganism such as a broken strain. The cell lysate may include, for example, a macromolecule such as DNA, RNA, protein, peptide, carbohydrate, lipid, etc., and/or a micromolecule such as amino acids, sugars, fatty acids, etc., or fractions thereof. In addition, the lysate may include cell debris, which may be smooth or granular.

Throughout the whole document, the term "extract" means a isolate separated from a culture medium of a strain. Also, an extract may include a fraction or a culture filtrate.

In general, strains used as probiotics are expected to have the same or similar effects on the strain itself, on the strain culture, on the strain lysate, and on the strain extract.

Soy protein used in the present disclosure will be described. The soy protein is one of plant proteins and contains various phytonutrients helpful in suppressing sarcopenia. Also, the soy protein is full of dietary fiber and lower in saturated fat and carbohydrates than animal proteins and thus known to be effective in weight control. Therefore, the soy protein has been used widely as a supplement as a plant protein source. Also, the soy protein is higher in some amino acids, such as arginine, phenylalanine, tryptophan, etc., than whey protein and thus essential to build muscle tissue. A steady intake of the soy bean can reduce a low-density lipoprotein (LDL) level in blood and increase a high-density lipoprotein (HDL) level in blood. Thus, the soy bean is known to be helpful in improving the cholesterol level. Further, the soy protein is cheaper than other plant proteins, such as pea protein and known to have no peculiar odor of plant-derived proteins.

A dietary protein including the soy protein is a polymer material and needs to be broken down into low molecular materials. In the body, peptide chains of protein are broken down by various digestive enzymes, such as pepsin in the stomach and trypsin and chymotrypsin in the small intestine, into finally amino acids and then absorbed by the villi of the small intestine. In this process, the enzymes secreted by intestinal microorganisms in the digestive system also influence the breakdown and absorption of protein. The intestinal microorganisms can secrete enzymes which cannot be biosynthesized by humans. Therefore, the types and amounts of amino acids produced by breakdown of a dietary protein may vary greatly depending on the composition of the intestinal microorganisms and the intake of probiotics.

Among amino acids produced by breakdown of protein, valine, isoleucine, and leucine, which are branched-chain amino acids (BCAA), are essential to maintain normal protein metabolic balance and synthesize muscle, and can reduce damage to muscle caused by exercise and promote. Particularly, leucine serves to transmit a signal in a muscle biosynthetic pathway and thus helps reduce sarcopenia in elderly people.

In addition to the BCAA, specific amino acids, such as glycine as a component of creatine which boots exercise performance, threonine which contributes to skeletal muscle synthesis, tyrosine which helps improve exercise performance, and lysine which helps grow skeletal muscle and suppress proteolysis, can increase muscle building and exercise performance.

In general, the soy protein is lower in amino acids including the BCAA than the whey protein and has a lower protein absorption rate than the whey protein. Thus, although the soy protein has been used widely as plant dietary protein, the soy protein is unsuitable for prompt muscle regeneration, prevention or relief of sarcopenia, etc. compared to the whey protein.

Therefore, it is expected that muscle regeneration can be achieved by intake of the soy protein as well as the whey protein as long as it is possible to promote digestion and breakdown of the soy protein and improve production of amino acids (BCAA, etc.) from the ingested soy protein.

Accordingly, the present inventors have developed a mixed strain of *Limosilactobacillus fermentum* LM1020 and *Lactobacillus acidophilus* LM1060 which is capable of overcoming the disadvantages upon intake of soy protein which has lower digestion and absorption rates and is lower in BCAA than whey protein. Further, under the provisions of the Budapest Treaty on the International Recognition of the Deposit of Microorganisms for the Purposes of Patent Procedure, strain *Limosilactobacillus fermentum* LM1020 was deposited with the international depositary authority: the Korean Culture Center of Microorganisms (KCCM) on Dec. 23, 2020 under the accession number KCCM12918P; and strain *Lactobacillus acidophilus* LM1060 was deposited with the international depositary authority: the Korean Culture Center of Microorganisms (KCCM) on Nov. 7, 2019 under the accession number KCCM12625P.

Hereinafter, examples of the present disclosure will be described in detail with reference to the accompanying drawings. However, the present disclosure may not be limited to the following examples and drawings.

An aspect of the present disclosure provides a mixed strain containing *Limosilactobacillus fermentum* LM1020 (Accession Number: KCCM12918P) *and Lactobacillus acidophilus* LM1060 (Accession Number: KCCM12625P), and the mixed strain is capable of improving the degree of soy protein proteolysis.

Another aspect of the present disclosure provides a composition containing the mixed strain in various forms as an active ingredient, and the various forms include one or more of the mixed strain or a culture, lysates and extracts of the mixed strain. Also, the composition includes a food composition, a health functional food composition, an infant formula composition, and a pharmaceutical composition for preventing or relieving.

Throughout the whole document, the term "food" may include meats, sausages, breads, chocolates, candies, snacks, cookies, pizza, ramens, other noodles, gums, dairy products including ice cream, soups, beverages, teas, drinks, alcohol drinks, vitamin complexes, health functional foods and health foods, and may include all foods in the accepted meaning.

The food of the present disclosure can be manufactured by conventional methods used in the art, and can be manufactured by adding conventional raw materials and ingredients used in the art. Further, a formulation of the food is not limited as long as the formulation is accepted as a food. The food composition of the present disclosure may be prepared in a variety of formulations. Since the food is used as raw materials, unlike general drugs, the food composition is free from side effects which may occur when a drug is taken for a long time, and may have excellent portability. Therefore, the food of the present disclosure may be taken as a supplement.

The food composition may further contain a physiologically acceptable carrier. The kind of the carrier is not particularly limited. Any carrier may be used as long as it is commonly used in the art.

Further, the food composition may further contain additional ingredients that are commonly used in food compositions so as to improve the smell, taste, look, etc. For example, the food composition may contain vitamins A, C, D, E, B1, B2, B6, B12, niacin, biotin, folate, pantothenic acid, etc. Furthermore, the food composition may also contain minerals such as zinc (Zn), iron (Fe), calcium (Ca), chromium (Cr), magnesium (Mg), manganese (Mn), copper (Cu), etc.

The food composition of the present disclosure may be used as, for example, a health beverage composition. In this case, the health beverage composition may further contain various natural carbohydrates or sweeteners, as in common beverages. The natural carbohydrates may include monosaccharides, disaccharides, polysaccharides, and sugar alcohols. The sweeteners may be natural sweeteners, such as thaumatin or a stevia extract, or synthetic sweeteners, such as saccharine or aspartame.

In addition, the health beverage composition may contain various nutrients, vitamins, minerals, flavors, colorants, pectic acid and salts thereof, alginic acid and salts thereof, organic acid, protective colloidal thickeners, pH regulators, stabilizers, antiseptics, glycerin, alcohols or carbonating agents. Moreover, the health beverage composition may contain fruit flesh used to prepare natural fruit juices, fruit juice beverages or vegetable beverages. These ingredients may be used individually or in combination.

Throughout the whole document, the term "health functional food" refers to foods prepared and processed using raw materials or ingredients having useful functions to the human body in accordance with the Health Functional Foods Act, No. 6727, and the term "functional" indicates a beneficial effect for human health, such as the regulation of nutrients for the structure and function of the human body, physiological action, etc.

The health food refers to a food having effects of actively maintaining or promoting health conditions, as compared with general foods, and a health supplement food refers to a food for supplementing health. If necessary, the health functional food, health food, and health supplement food may be interchangeably used with each other. Specifically, the health functional food is a food prepared by adding the mixed strain composition of the present disclosure to food materials, such as beverages, teas, spices, gums, confectionery, etc., or formulated as capsules, powders, suspensions, etc. The functional health food means that it takes a specific effect on health when consumed, but unlike general drugs, the health functional food is free from side effects that may occur when a drug is taken for a long time since the food is used as raw materials.

Throughout the whole document, the term "pharmaceutical composition" may be formulated as oral medications, such as powders, granules, tablets, capsules, suspensions, emulsions, syrup, aerosol, etc., ointment, suppositories or sterile injectable solutions, according to conventional methods. However, the present disclosure is not limited thereto.

The pharmaceutical composition according to an embodiment of the present disclosure may be a drug composition or a quasi-drug composition.

Throughout the whole document, the term "quasi-drug" refers to an article having a milder action than drugs, among articles being used for the purpose of diagnosis, treatment, improvement, alleviation, handling or prevention of human or animal diseases. For example, according to the Pharmaceutical Affairs Law, the quasi-drugs are those, excluding articles used as drugs, including articles used for the purpose of treating or preventing human or animal diseases and articles which have a mild action on or have no direct influence on the human body.

In an embodiment of the present disclosure, the pharmaceutical composition may be administered in a pharmaceutically effective amount. Throughout the whole document, the term "pharmaceutically effective amount" refers to an amount sufficient to treat or prevent diseases at a reasonable benefit/risk ratio applicable to any medical treatment or prevention. An effective dosage level may be determined depending on factors including severity of the disease, drug activity, a patient's age, body weight, health conditions, gender, sensitivity to the drug, administration time, administration route, and excretion rate of the composition of the present disclosure, duration of treatment, drugs blended with or co-administered with the composition of the present disclosure, and other factors known in the medical field. The pharmaceutical composition of the present disclosure may be administered individually or in combination with an ingredient known for treating intestinal diseases. It is important to administer an amount to obtain a maximum effect in a minimum amount without side effects by considering all of the above-described factors.

The pharmaceutical composition of the present application may be administered via, but not particularly limited to, intraperitoneal administration, intravenous administration, intramuscular administration, subcutaneous administration, intradermal administration, transdermal patch administration, oral administration, intranasal administration, intrapulmonary administration, rectal administration, etc. depending on the purpose. However, when the pharmaceutical composition is administered via oral administration, it can be administered in an unformulated form, and since the mixed strain of the present disclosure can be denatured or degraded by gastric acid, the composition for oral administration may be coated with an active drug, formulated to be protected from degradation in the stomach, or formulated in the form or an oral patch. Also, the composition may be administered by any device capable of delivering an active ingredient to a target cell.

MODE FOR CARRYING OUT THE INVENTION

Example 1. Selection of Strain Having Excellent Soy Protein Proteolysis

Culture media were prepared from soy protein isolates to select strains capable of greatly improving the degree of soy protein proteolysis and then, the degree of soy protein proteolysis of each strain was identified. As for the soy protein culture media, 10 g of soy protein isolate powder and 1 g of glucose were dissolved in 1 L of distilled water, aliquoted into 15 mL conical tubes with 10 mL each and sterilized, followed by cooling at room temperature. A bromelain solution was used as a positive control group, which was prepared and used by dissolving bromelain in an acetate buffer of pH 4.5 at 5% w/v.

The strains used for strain selection were as shown in Table 1 and used to evaluate the degree of proteolysis after cultured three times in 12-hour intervals. The inoculum concentration for each culture was 0.1% v/v, and the strain culture temperature was adjusted to $37\pm3°$ C. After culture, the cultured strains were recovered by centrifugation (10,000 rpm, 10 min) of the culture media for the respective strains and washed twice with phosphate buffered saline, followed by dissolving the cultured strains in phosphate buffered saline to 8 log CFU/mL to prepare samples.

The prepared samples of the cultured strains were inoculated at 100 μL into 10 mL of the soy protein culture media, and the protein was quantified. Also, after the prepared samples were cultured in an incubator at $37\pm3°$ C. for 48 hours, the protein was quantified to compare the amounts of protein before and after culture, followed by evaluation of the degree of soy protein proteolysis of each strain.

Protein contents were measured by using a BCA assay kit. Standards were prepared by dissolving 2 mg of bovine serum albumin in 1 mL of distilled water and then diluted with distilled water to 1 mg/mL, 0.5 mg/mL, 0.25 mg/mL, and 0.125 mg/mL so as to be used as standards for respective concentrations together with distilled water (0 mg/mL). Also, 100 µL of each of the culture media was collected and then diluted with 900 µL of distilled water (10-fold) so as to be used as samples of the culture media. Then, 0 mg/mL to 2 mg/mL standards and diluted samples of the culture media were aliquoted into a 96-well plate with 20 µL each and treated with 160 µL of a BCA reagent in the kit, followed by dark reaction in an incubator at 37±3° C. for 30 minutes. Then, the absorbance was measured at 560 mm. A standard curve was plotted based on the results of absorbance for respective concentrations of the standards, and the absorbance values of the respective culture media were fit to the standard curve to measure the protein contents. The degree of proteolysis was obtained by multiplying a value, which was obtained by subtracting a quantitative value of protein after 48-hour culture from a quantitative value of protein before culture, by 100. In the following tables of the present disclosure, "–" represents 0.

Degree of proteolysis (%)=(A–B)×100

A: Quantitative value of protein before culture

B: Quantitative value of protein after 48-hour culture

As a result of comparing the degree of soy protein proteolysis of various strains under the same conditions, it was confirmed that not all of the strains can break down the soy protein and the strains exhibit different degrees of proteolysis. It was confirmed that among the strains used for evaluation, *Lactobacillus acidophilus* LM1060, which is LP2, and *Limosilactobacillus fermentum* LM1020, which is LP7, exhibit higher degrees of soy protein proteolysis than the strains belonging to other genera. Particularly, it was confirmed that *Limosilactobacillus fermentum* LM1020 exhibits a higher degree of proteolysis than *Limosilactobacillus fermentum*, which is LP6, belonging to the same genus (Table 2).

TABLE 1

Strains used for comparison of degree of soy protein proteolysis

| Abbreviation | Strain | Origin |
|---|---|---|
| ATCC 53103 | *Lacticaseibacillus rhamnosus* | Human body |
| LP1 | *Lactobacillus gasseri* | Human breast milk |
| LP2 | *Lactobacillus acidophilus* LM1060 | Adult feces |
| LP3 | *Lactiplantibacillus plantarum* | Kimchi |
| LP4 | *Lactiplantibacillus reuteri* | Human breast milk |
| LP5 | *Lactiplantibacillus reuteri* | Adult feces |
| LP6 | *Limosilactobacillus fermentum* | Cheese |
| LP7 | *Limosilactobacillus fermentum* LM1020 | Fermented dough |

TABLE 2

| Classification | Soy protein proteolysis index (%) |
|---|---|
| Positive Control Group - 5% bromelain | 20.42 ± 0.50 |
| ATCC 53103 | 14.40 ± 3.27 |
| LP1 | 13.96 ± 3.62 |
| LP2 | 14.41 ± 2.08 |
| LP3 | 14.20 ± 1.96 |
| LP4 | 8.86 ± 0.63 |
| LP5 | — |
| LP6 | — |
| LP7 | 17.40 ± 0.50 |

Comparison of Probiotics in Terms of Soy Protein Proteolysis Index

Example 2. Verification of Ability to Produce Valine, Isoleucine, and Leucine

After a mixed composition of *Limosilactobacillus fermentum* LM1020 and *Lactobacillus acidophilus* LM1060 was cultured with the soy protein, changes in content of branched chain amino acids (valine, isoleucine, and leucine) produced by breakdown of the soy protein were analyzed by using high-performance liquid chromatography with photodiode array detection.

The strains were cultured three times in the same manner as in Example 1 and then, the cultured strains were recovered and inoculated as a single or mixed strain into soy protein culture media, followed by culture in an incubator at 37±3° C. for 72 hours. Then, the supernatants obtained by centrifugation (4,000 rpm, 15 min) of the culture media were used as analytical samples.

After 5 mL of each of the analytical samples was put into a test tube and concentrated at 110° C. under a nitrogen environment and finely ground, the resultant product was dissolved in 1 mL of a 0.1 N aqueous hydrochloric acid solution, followed by homogenization through vortexing. Then, free amino acids were extracted from the concentration sample in an ultrasonic water bath for 15 minutes. The free amino acid extraction fluid was centrifuged to filter the supernatant through a filter. The free amino acids were analyzed by using high-performance liquid chromatography with photodiode array detection. The analysis was performed with an gradient elution by using a 0.1% aqueous formate solution and a 0.1% formate acetonitrile solution as a mobile phase, and an Agilent Zorbax Eclipse AAA column (4.6 mm ID*150 mm, 5 µm) was used for analysis. Then, the predictive values of synergistic effects were calculated using Colby's formula and then compared with measured values.

As a result, it was confirmed that the ability to produce valine, isoleucine, and leucine is improved by mixing two strains at all of mixing ratios (CFU ratio) except some mixing ratios for valine, compared to a case where a single strain was used (FIG. 1, Table 3).

TABLE 3

Comparison of ability to produce BCAA depending on mixing ratio of *Limosilactobacillus fermentum* LM1020 and *Lactobacillus acidophilus* LM1060

| A[1] | B[2] | Measurement value (µg/mL) | | | | Prediction value (µg/mL) | | | |
|---|---|---|---|---|---|---|---|---|---|
| | | Valine | Isoleucine | Leucine | Total | Valine | Isoleucine | Leucine | Total |
| 100% | 0% | 24.9 | 22.4 | 17.7 | 65.0 | — | — | — | — |
| 90% | 10% | 72.6 | 188.3 | 127.2 | 388.0 | 24.3 | 22.5 | 17.2 | 64.0 |
| 80% | 20% | 91.0 | 302.9 | 183.1 | 577.0 | 23.8 | 22.7 | 16.8 | 63.3 |
| 70% | 30% | 49.0 | 231.0 | 134.4 | 414.3 | 23.4 | 23.0 | 16.5 | 62.9 |

TABLE 3-continued

Comparison of ability to produce BCAA depending on mixing ratio of *Limosilactobacillus fermentum* LM1020 and *Lactobacillus acidophilus* LM1060

| A[1] | B[2] | Measurement value (μg/mL) | | | | Prediction value (μg/mL) | | | |
|---|---|---|---|---|---|---|---|---|---|
| | | Valine | Isoleucine | Leucine | Total | Valine | Isoleucine | Leucine | Total |
| 60% | 40% | 63.5 | 262.0 | 167.4 | 492.8 | 23.2 | 23.4 | 16.2 | 62.9 |
| 50% | 50% | 0.0 | 210.0 | 115.9 | 325.9 | 23.0 | 24.0 | 16.0 | 63.1 |
| 40% | 60% | 7.9 | 345.8 | 165.1 | 590.2 | 23.0 | 24.7 | 15.9 | 63.6 |
| 30% | 70% | 60.5 | 278.4 | 131.4 | 470.2 | 23.1 | 25.5 | 15.8 | 64.4 |
| 20% | 80% | 51.8 | 260.5 | 129.2 | 441.5 | 23.4 | 26.5 | 15.7 | 65.6 |
| 10% | 90% | 56.5 | 243.2 | 131.4 | 431.0 | 23.7 | 27.6 | 15.7 | 67.0 |
| 0% | 100% | 24.2 | 28.8 | 15.8 | 68.8 | — | — | — | — |

[1]*Limosilactobacillus fermentum* LM1020
[2]*Lactobacillus acidophilus* LM1060

Example 3. Verification of Ability to Produce Threonine, Glycine, Tyrosine, and Lysine After a mixed composition of *Limosilactobacillus fermentum* LM1020 and *Lactobacillus acidophilus* LM1060 was cultured with the soy protein, changes in content of free amino acids produced by breakdown of the soy protein were analyzed in the same manner as in Example 2 by using high-performance liquid chromatography with photodiode array detection. Then, the predictive values of synergistic effects were calculated using Colby's formula and then compared with measured values.

Figure 2:
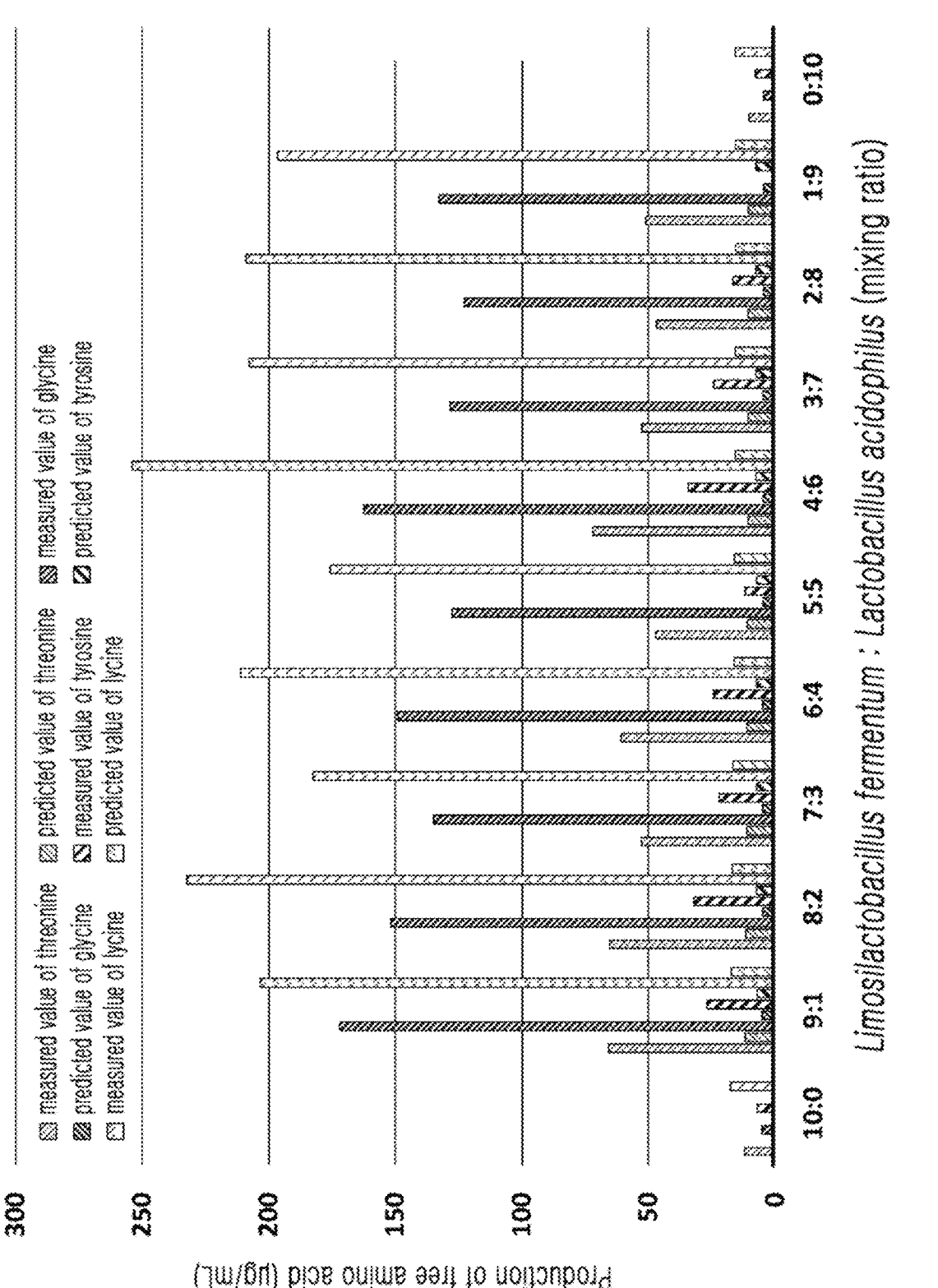
FIG. 2 shows the result of confirming that a mixed strain of the present disclosure has the ability to produce threonine, glycine, tyrosine, and lysine for each mixing ratio, according to Example 3.

As a result, it was confirmed that the ability to produce threonine, glycine, tyrosine, and lysine is improved at all of mixing ratios (CFU ratio) except some mixing ratios for tyrosine, compared to a case where a single strain was used (FIG. 2, Table 4).

TABLE 4

Comparison of ability to produce threonine, glycine, tyrosine, and lysine depending on mixing ratio of *Limosilactobacillus fermentum* LM1020 and *Lactobacillus acidophilus* LM1060

| A[1] | B[2] | Measurement value (μg/mL) | | | | Prediction value (μg/mL) | | | |
|---|---|---|---|---|---|---|---|---|---|
| | | Threonine | Glycine | Tyrosine | Lysine | Threonine | Glycine | Tyrosine | Lysine |
| 100% | 0% | 12.2 | 5.2 | 7.2 | 17.7 | — | — | — | — |
| 90% | 10% | 66.0 | 172.2 | 26.9 | 203.4 | 11.9 | 5.1 | 7.2 | 17.2 |
| 80% | 20% | 65.5 | 151.6 | 32.1 | 232.4 | 11.6 | 5.0 | 7.3 | 16.8 |
| 70% | 30% | 52.7 | 134.8 | 22.2 | 182.5 | 11.4 | 5.0 | 7.3 | 16.5 |
| 60% | 40% | 60.6 | 149.2 | 24.4 | 211.1 | 11.2 | 4.9 | 7.3 | 16.2 |
| 50% | 50% | 47.1 | 127.6 | 11.9 | 175.8 | 11.0 | 4.8 | 7.4 | 16.0 |
| 40% | 60% | 72.1 | 162.5 | 34.3 | 254.0 | 10.8 | 4.8 | 7.5 | 15.9 |
| 30% | 70% | 52.5 | 128.3 | 24.2 | 207.9 | 10.7 | 4.7 | 7.5 | 15.8 |
| 20% | 80% | 46.8 | 122.8 | 16.8 | 209.0 | 10.6 | 4.7 | 7.6 | 15.7 |
| 10% | 90% | 51.1 | 132.7 | 0.0 | 196.5 | 10.5 | 4.6 | 7.7 | 15.7 |
| 0% | 100% | 10.5 | 4.6 | 7.8 | 15.8 | — | — | — | — |

[1]*Limosilactobacillus fermentum* LM1020
[2]*Lactobacillus acidophilus* LM1060

In sum, it was confirmed that the mixed strain of the present disclosure or the composition containing a culture of the mixed strain can improve the degree of proteolysis and also improve the ability to produce valine, leucine, and isoleucine, which are branched chain amino acids, or threonine, glycine, tyrosine, and lysine.

We claim:

1. A composition, comprising:
a mixed strain including *Limosilactobacillus fermentum* LM1020 deposited under accession number KCCM12918P and *Lactobacillus acidophilus* LM1060 deposited under accession number KCCM12625P, wherein the mixed strain is capable of improving soy protein proteolysis.

2. A composition, comprising:
a mixed strain including *Limosilactobacillus fermentum* LM1020 deposited under accession number KCCM12918P and *Lactobacillus acidophilus* LM1060 deposited under accession number KCCM12625P, wherein the mixed strain improves the ability to produce amino acids.

3. The composition of claim 2,
wherein the amino acids include one or more selected from the group consisting of isoleucine, leucine, threonine, glycine, and lysine, and the mixed strain has a mixing ratio of *Limosilactobacillus fermentum* LM1020:*Lactobacillus acidophilus* LM1060 of 9:1 to 1:9.

4. The composition of claim 3,
wherein the amino acids further include valine, and
the mixed strain has a mixing ratio of *Limosilactobacillus fermentum* LM1020:*Lactobacillus acidophilus* LM1060 of 9:1 to 6:4 or 3:7 to 1:9.

5. The composition of claim 3,
wherein the amino acids further include tyrosine, and
the mixed strain has a mixing ratio of *Limosilactobacillus fermentum* LM1020:*Lactobacillus acidophilus* LM1060 of 9:1 to 2:8.

6. The composition of claim 3,
wherein the amino acids further include valine and tyrosine and the mixed strain has a mixing ratio of *Limosilactobacillus fermentum* LM1020:*Lactobacillus acidophilus* LM1060 of 9:1 to 6:4 or 3:7 to 2:8.

7. A food composition containing one or more of the mixed strain of claim 1 or a culture, lysates, and extracts of the strain as active ingredients.

8. A health functional food composition containing one or more of the mixed strain of claim 1 or a culture, lysates, and extracts of the strain as active ingredients.

9. An infant formula composition containing one or more of the mixed strain of claim 1 or a culture, lysates, and extracts of the strain as active ingredients.

10. A pharmaceutical composition for preventing or relieving sarcopenia, containing one or more of the mixed strain of claim 1 or a culture, lysates, and extracts of the strain as active ingredients.

11. A food composition containing one or more of the mixed strain of claim 2 or a culture, lysates, and extracts of the strain as active ingredients.

12. A health functional food composition containing one or more of the mixed strain of claim 2 or a culture, lysates, and extracts of the strain as active ingredients.

13. An infant formula composition containing one or more of the mixed strain of claim 2 or a culture, lysates, and extracts of the strain as active ingredients.

14. A pharmaceutical composition for preventing or relieving sarcopenia, containing one or more of the mixed strain of claim 2 or a culture, lysates, and extracts of the strain as active ingredients.

* * * * *